(12) United States Patent
Dodge et al.

(10) Patent No.: US 8,720,008 B2
(45) Date of Patent: May 13, 2014

(54) HORIZONTALLY ADJUSTABLE HINGE FOR USE WITH HEAVY INSULATED DOORS

(76) Inventors: Timothy David Dodge, Whitehall, PA (US); Matthew James Vassallo, Allentown, PA (US)

( * ) Notice: Subject to any disclaimer, the term of this patent is extended or adjusted under 35 U.S.C. 154(b) by 0 days.

(21) Appl. No.: 13/476,461

(22) Filed: May 21, 2012

(65) Prior Publication Data

US 2013/0305488 A1 Nov. 21, 2013

(51) Int. Cl.
*E05D 7/04* (2006.01)
(52) U.S. Cl.
USPC .................. 16/245; 16/236; 16/246; 16/387
(58) Field of Classification Search
USPC ........... 16/245, 235, 238, 246, 236, 237, 387, 16/270–272
See application file for complete search history.

(56) References Cited

U.S. PATENT DOCUMENTS

| | | | | |
|---|---|---|---|---|
| 928,760 | A * | 7/1909 | Hunter | 16/238 |
| 2,583,950 | A * | 1/1952 | Kirschner | 16/238 |
| 2,854,687 | A * | 10/1958 | Baldauf | 16/236 |
| 3,932,913 | A * | 1/1976 | Johnson | 16/245 |
| 4,696,078 | A * | 9/1987 | Stromquist | 16/301 |
| 4,905,347 | A * | 3/1990 | Wroth | 16/308 |
| 5,713,105 | A * | 2/1998 | Toomey | 16/245 |
| 7,334,296 | B2 * | 2/2008 | Park | 16/330 |
| 7,584,523 | B1 * | 9/2009 | Finkelstein et al. | 16/260 |
| 7,945,996 | B2 * | 5/2011 | Gunderson | 16/312 |
| 2004/0128794 | A1 * | 7/2004 | Chung | 16/236 |

FOREIGN PATENT DOCUMENTS

| | | | |
|---|---|---|---|
| DE | 3719516 A1 | * | 12/1988 |
| EP | 285229 A2 | * | 10/1988 |
| FR | 2640734 A1 | * | 6/1990 |
| GB | 2407845 A | * | 5/2005 |
| JP | 2010275710 A | * | 12/2010 |

* cited by examiner

*Primary Examiner* — Chuck Mah
(74) *Attorney, Agent, or Firm* — Oakwood Law Group, LLP; Jie Tan

(57) ABSTRACT

A hinge for use with an insulated door of a walk-in freezer, refrigerator or cooler including a hinge base adapted to be attached to the frame of said freezer, refrigerator or cooler, a hinge blade pivotally coupled to the hinge base and a wall that extends across the hinge base which has a U shaped clearance opening. Fastening screws located in clearance openings in the hinge blade and threadedly coupled to a door mounting plate adapted to be securely attached to the insulated door for slidably or securely coupling the hinge blade to the door mounting plate, and a micro adjust screw having a threaded shaft located in the U shaped clearance opening and threadedly coupled to the door mounting plate, wherein turning the micro adjust screw slides the door mounting plate horizontally along the hinge blade to provide door lift or rotation to compensate for frame or mounting misalignment.

18 Claims, 3 Drawing Sheets

HORIZONTALLY ADJUSTABLE HINGE FOR USE WITH HEAVY INSULATED DOORS

BACKGROUND OF THE INVENTION

1. Field of the Invention

The present invention relates generally to a hinge for use with heavy insulated doors which are used with walk in freezers or refrigerators and more specifically to a hinge which can quickly and easily be adjusted horizontally to provide door lift and rotation to compensate for frame or mounting misalignment by means of a screw which is accessible.

2. Description of Related Art

A hinge for use with an insulated freezer door is known in the prior art. More specifically, by way of example, U.S. Pat. No. 7,870,642 to Finkelstein, et al. discloses an anti-sag hinge having a mounting flange which is mounted to a jamb and a strap assembly which is mounted to a door and pivotally coupled to the mounting flange. The strap assembly has a strap with a plurality of screw openings, an adjustment bracket having a plurality of screw openings configured to be alignable with the strap screw openings, and a lateral adjuster which causes lateral relative movement between the strap and the adjustment bracket.

U.S. Pat. No. 7,584,523 to Finkelstein, et al. discloses an anti-sag hinge having a flange assembly having a mounting flange, a lower hinge barrel and an upper hinge barrel. The upper hinge barrel is removably mounted to the mounting flange. The hinge also has a strap assembly pivotally coupled to the flange assembly. The strap assembly includes a strap and a cylinder portion removably coupled to the lower hinge barrel and the upper hinge barrel.

U.S. Pat. No. 7,055,214 to Finkelstein discloses a mounting flange adapted to be mounted to a jamb, the mounting flange having an exterior facing surface having a select texture and a strap assembly which is mounted to a door and pivotally coupled to the mounting flange. The hinge further includes a mounting flange adjustment plate having a plurality of screw openings there through which are alignable with mounting flange screw openings and has an interior facing surface with a select texture which is mateably in different positions with the mounting flange exterior facing surface select texture.

U.S. Pat. No. 6,374,458 to Finkelstein discloses an internal adjustment plate to combat misalignment or sag in the door of a commercial reach-in freezer. A mounting bracket, a strap assembly, and an adjustment plate cooperate to mount a refrigerator or freezer door and, when sagging occurs, provides for correction by manipulation of the adjustment plate to realign the door within the jamb of the freezer cabinet jamb.

SUMMARY OF THE INVENTION

In an exemplary embodiment of the present invention there is disclosed a hinge for use with an insulated door of a walk in freezer or refrigerator comprises:

a hinge base adapted to be attached to the frame of a walk in freezer or refrigerator;

a hinge blade pivotally coupled to the hinge base and having a cavity in its bottom side wherein one wall of the cavity extends across the hinge base and has a U shaped clearance opening;

a door mounting plate adapted to be securely attached to the insulated door;

fastening screws located in clearance openings in the hinge blade threadedly coupled to the door mounting plate for coupling the hinge blade to the door mounting plate; and a micro adjust screw having a threaded shaft located in the U shaped clearance opening and threadedly coupled to the door mounting plate;

wherein turning the micro adjust screw slides the door mounting plate horizontally along the hinge blade to provide door lift or rotation to compensate for frame or mounting misalignment;

wherein tightening the fastening screws locks the hinge blade to the door mounting plate.

In another exemplary embodiment of the present invention there is disclosed a method for adjusting a hinge for providing door lift or rotation to compensate for frame or mounting misalignment of an insulated door of a walk in freezer or refrigerator comprising:

providing a hinge base adapted to be attached to the frame of a walk in freezer or refrigerator;

providing a hinge blade pivotally coupled to the hinge base and having a cavity in its bottom side wherein one wall of the cavity extends across the hinge base and has a U shaped clearance opening;

providing a door mounting plate adapted to be securely attached to the insulated door;

locating fastening screws in clearance openings in the hinge blade threadedly coupled to the door mounting plate for coupling the hinge blade to the door mounting plate; and providing a micro adjust screw having a threaded shaft located in the U shaped clearance opening and threadedly coupled to the door mounting plate;

wherein turning the micro adjust screw slides the door mounting plate horizontally along the hinge blade to provide door lift or rotation to compensate for frame or mounting misalignment;

wherein tightening the fastening screws locks the hinge blade to the door mounting plate.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

DESCRIPTION OF THE PREFERRED EMBODIMENT

Figure 1:
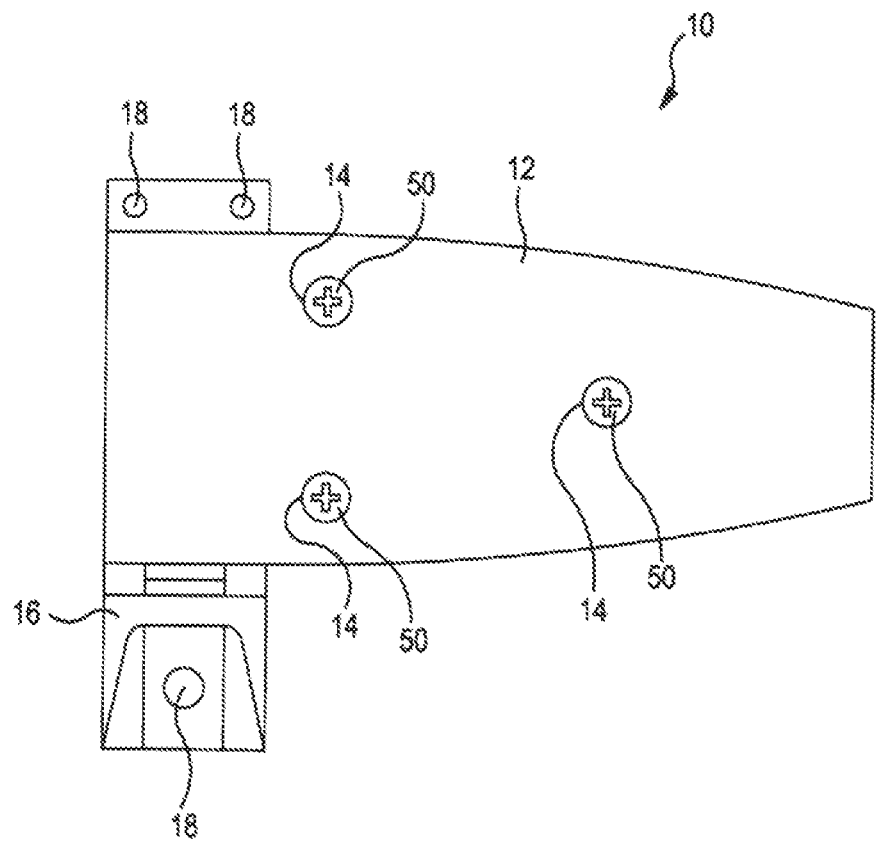
FIG. 1 is a top view of the horizontally adjustable hinge for use with heavy insulated doors in accordance with the principles of the invention.

Referring to FIG. 1, there is disclosed a top view of the horizontally adjustable hinge 10 for use with heavy insulated walk in freezer doors in accordance with the principles of the invention. The hinge 10 includes a hinge blade 12 which has three countersunk clearance openings 14 sized to receive three fastening screws 50 designed to receive an adjusting tool, such as a screw driver which is used to attach the hinge blade to a door mounting plate adapted to be attached to a heavy insulated door of, for example, a walk in freezer or refrigerator. The hinge blade is rotatably coupled to a hinge base 16 which is adapted to be securely attached to the frame of a walk in freezer or refrigerator with three fastening bolts that pass through countersunk openings 18 in the hinge base and the frame of the walk in freezer or refrigerator.

Figure 2:
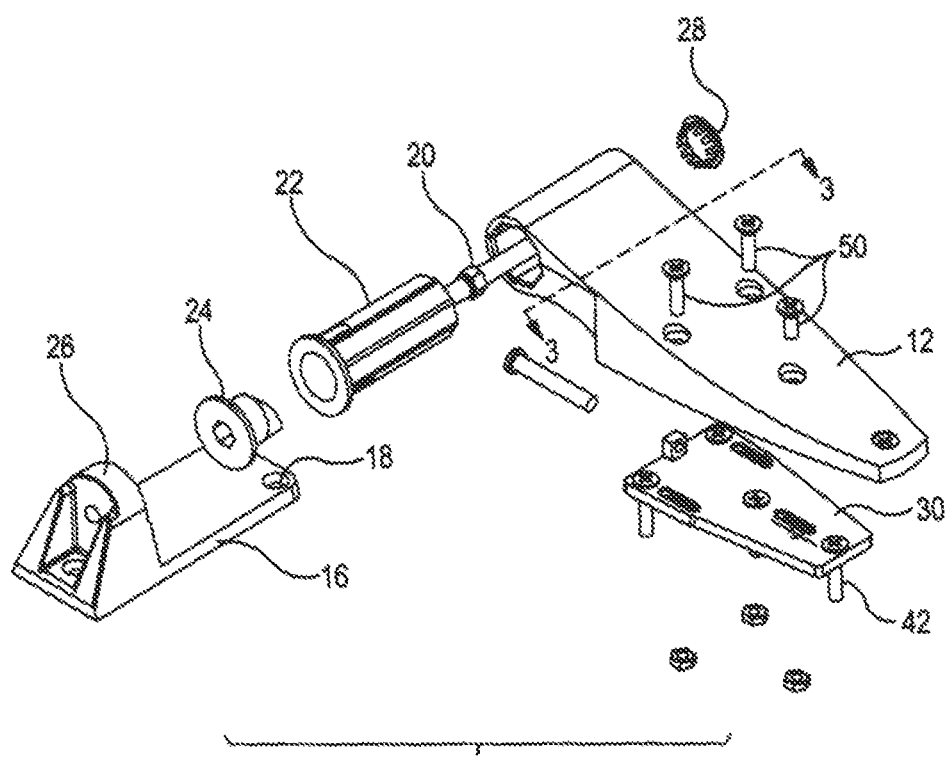
FIG. 2 is an exploded view of the horizontally adjustable hinge of FIG. 1 for use with heavy insulated doors showing the hinge blade located above the door mounting plate and parts of the hinge base in accordance with the principles of the invention.

Looking at FIG. 2, there is shown an exploded view of the horizontally adjustable hinge 10 for use with heavy insulated doors where the hinge blade is located above the door mounting plate and the hinge base is coupled to the hinge blade in accordance with the principles of the invention. The hinge base 16 is rotatably coupled to the hinge blade 12 with a hinge pin 20 which passes through a female cam 22 and a male cam 24 that cooperates with the female cam, and is attached to flange 26 which is a part of the hinge base and provides a support for the hinge blade. A spring acting in compression, not shown, may be located around the female cam to press down onto the male cam to urge the hinge blade to swing to a closed position relative to the hinge base. A cap plug 28 is located on the top of the hinge blade and covers the top of the hinge pin 20. A door mounting plate 30 which is coupled to the hinge blade is adapted to be securely attached to a heavy insulated door with fastening screws and nuts.

Figure 3:
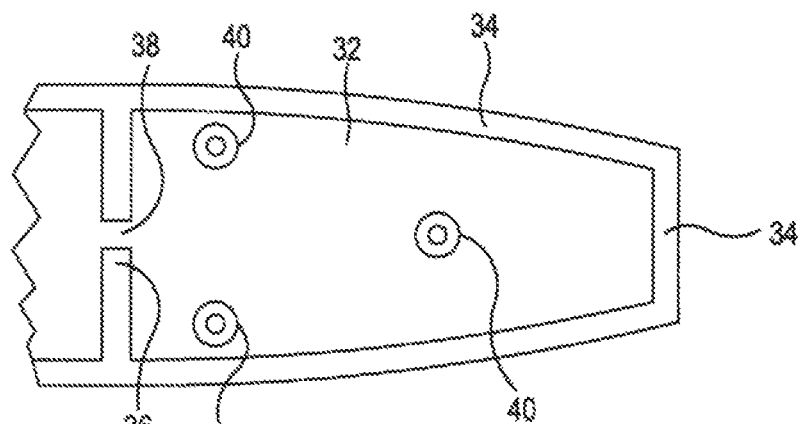
FIG. 3 is a plan view along the line 3-3 of FIG. 2 showing the bottom of the hinge blade without the door plate.

Referring to FIG. 3, there is shown a plan view along the line 3-3 of FIG. 2 showing a portion of the underside of the hinge blade, absent the door mounting plate, which has a cavity formed by three shallow walls 34 located around the perimeter of the hinge blade and a cross wall 36 having a centrally located U shaped cutout 38 where the cavity is configured to receive the door mounting plate. Located within the cavity are three bosses 40 which include countersunk openings 14. Cavity 32 is configured to receive the door mounting plate 30.

Figure 4:
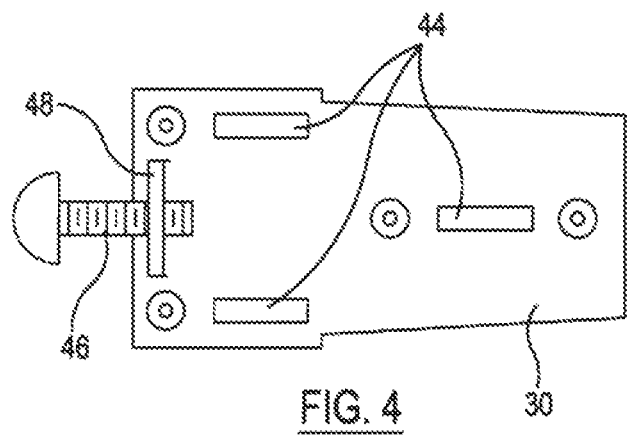
FIG. 4 is plan view of the door mounting plate including a micro adjust screw located in a U shaped slot in the hinge blade for slidably positioning the door mounting plate relative to the hinge blade.

Referring to FIG. 4, there is shown is plan view of the top side of the door mounting plate 30. The door mounting plate which is located in the cavity 32 of the hinge blade has a micro adjust screw 46 which engages a U shaped slot in the hinge blade for slidably positioning the door mounting plate relative to the hinge blade. The top side of the door mounting plate is flipped over and faces the bottom side of the cavity of the door blade. The top side of the door mounting plate contains four countersunk clearance openings for receiving door mounting hardware screws, see FIG. 2. Located in plate 30 are three slots 44 which are aligned with three countersunk openings located in the hinge blade. The hinge blade is slidably attached to the door mounting plate with fastening screws which pass through the countersunk openings in the hinge blade and the slots 44 in the door mounting plate, and are locked to each other when nuts on the ends of the fastening screw are tightened. The material around the slots 44 on the bottom side of the door mounting plate is removed to form a channel for receiving nuts which are threaded onto the hinge blade to adjustable plate screws 50. The channels allow the nuts to be recessed within the door mounting plate and prevent the nuts from turning as the fastening screws are being loosened or tightened. The micro adjust screw 46 which is adapted to receive an adjusting tool such as a screw driver is threaded into a protrusion 48 which is an integral part of and is perpendicularly oriented on the top side of the door plate 50 mounting surface.

Figure 5:
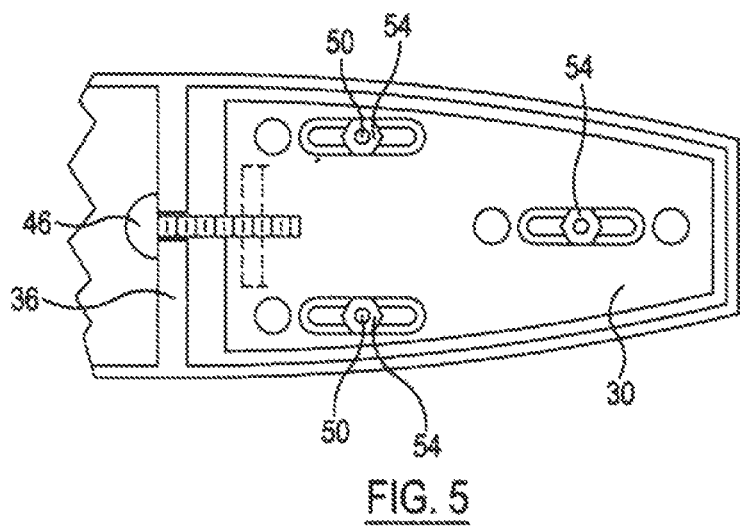
FIG. 5 is a view of the bottom of the hinge blade attached to the door mounting plate

Looking at FIG. 5, there is shown a view of the bottom of the hinge blade attached to the door mounting plate. The door mounting plate 30 is located within the cavity 32 and is slidably attached to the door blade 12 with fastening screws 50 and nuts 54. The micro adjust screw 46 is located in the U shaped cutout 38 of the cross wall 36. When the micro adjust screw is turned in one direction the door mounting plate is urged to move to the left relative to the hinge blade and when the micro adjust screw is turned in the other direction the hinge blade is urged to move to the right relative to the hinge blade.

In operation, the hinge base 16 is securely attached to the frame of a walk in freezer or refrigerator with three fastening bolts that pass through openings in the hinge base and are securely coupled to the door frame. Using shims and a bubble level, the door is squared up and adjusted to freely open and close in the walk in freezer or refrigerator frame without interference. The door mounting plate, which has been aligned with the hinge blade, is positioned with its bottom surface against the door and is permanently and securely attached to the outside surface of the door with four plate to door mounting hardware screws 42, see FIG. 2, which pass through countersunk openings in the door mounting plate. Prior to mounting the plate to the door, nuts 54, which thread onto the hinge blade to adjustable plate screws 50, are placed in the channels which allow the nuts to be recessed within the door mounting plate and prevents the nuts from turning as the fastening screws are being loosened or tightened. After the door mounting plate is securely attached to the outside surface of the freezer door, the hinge blade is positioned over the door mounting plate with the clearance openings for the threaded fasteners being positioned over the slots 44 and the threaded shaft of the micro adjust screw being located in the U shaped cutout 38. With the hinge blade of the hinge in its closed position, the head of the micro adjust screw 46 can be turned either clockwise or counter clockwise with an adjusting tool such as a Phillips head screw driver which is inserted between the hinge base 16 and the hinge blade 12. At this time the micro adjust screw is turner either clockwise or counter clockwise until the micro adjust screw is snug against the cross wall 36, and then the fastening screws 50 are inserted into clearance openings in the hinge blade and threaded into the nuts which are held captive in the channels and slots 44. After each of the hinges has been securely attached to the frame and door of the freezer or refrigerator, the shims can be removed.

As time goes by and the freezer door sags, it can be easily and quickly adjusted by loosening the fastening screws 50 on each hinge, repositioning the freezer door to be square and free to open and close, turning the micro adjust screw on each hinge with an adjusting tool such as, for example, a Phillips head screw driver which is inserted between the hinge base and the hinge blade until its head is snug against the cross wall 36, and then tightening the three fastening screws of each hinge blade to the adjustable plate.

With this invention the micro adjust screw is concealed from view and is readily accessible when the freezer door needs to be adjusted without opening the freezer door or disassembling or removing a part of the hinge.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed. Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

What is claimed is:

1. A hinge for use with an insulated door of a walk in freezer or refrigerator comprises:
   a hinge base adapted to be attached to the frame of a walk in freezer or refrigerator;
   a hinge blade pivotally coupled to the hinge base, said hinge blade having a cavity in its bottom side and a plurality of clearance openings formed therein, wherein a wall extends across the cavity and has a U shaped cutout;
   a door mounting plate adapted to be securely attached to the insulated door and having a plurality of slots for slidably receiving fastening screws;
   a plurality of fastening screws respectively located in the clearance openings in the hinge blade, said fastening screws extending through the slots of the mounting plate and threadedly coupled to captive nuts, for adjustably coupling the hinge blade to the door mounting plate; and
   a micro adjust screw having a threaded shaft located in the U shaped cutout, wherein said micro adjust screw is threadedly coupled to the door mounting plate via the threaded shaft such that loosening the fastening screws and turning the micro adjust screw against said wall causes the door mounting plate to slide horizontally along the hinge blade to provide door lift or rotation to compensate for frame or mounting misalignment; and
   wherein tightening the fastening screws locks the hinge blade to the door mounting plate.

2. The hinge of claim 1 wherein each of the slots for slidably receiving the fastening screws is inscribed in a channel formed in the bottom side of the door mounting plate, and each of the channels holds one of the captive nuts that thread onto the fastening screws.

3. The hinge of claim 2 wherein the channels in the bottom side of the door mounting plate prevent the nuts that thread onto the fastening screws from turning as the fastening screws are tightened or loosened.

4. The hinge of claim 3 wherein the micro adjust screw has a head attached to the threaded shaft, the head of the micro adjust screw is adapted to receive an adjusting tool.

5. The hinge of claim 4 wherein the head of the micro adjust screw is accessible with an adjusting tool inserted between the hinge base and the hinge blade.

6. The hinge of claim 5 wherein the head of the micro adjust screw is not visible from the top of the hinge or when in normal use.

7. The hinge of claim 5 wherein the head of the micro adjust screw is accessible without disassembling the hinge.

8. The hinge of claim 6 wherein the micro adjust screw is threadedly coupled to a perpendicularly oriented protrusion which projects out from a surface of the door mounting plate.

9. The hinge of claim 8 wherein the perpendicularly oriented protrusion projects out from the top surface of the door mounting plate.

10. A method for adjusting a hinge for providing door lift or rotation to compensate for frame or mounting misalignment of an insulated door of a walk in freezer or refrigerator comprising:
   providing a hinge base and attaching the hinge base to the flame of a walk in freezer or refrigerator;
   providing a hinge blade pivotally coupled to the hinge base, said hinge blade having a cavity in its bottom side and a plurality of clearance openings formed therein, wherein a wall extends across the cavity and has a U shaped cutout;
   providing a door mounting plate having a plurality of slots for slidably receiving fastening screws, and attaching the door mounting plate securely to the insulated door;
   locating a plurality of fastening screws respectively in the clearance openings in the hinge blade, inserting said fastening screws through the slots of the mounting plate and threadedly coupling the fastening screws to captive nuts; and
   providing a micro adjust screw having a threaded shaft and locating the micro adjust screw in the U shaped cutout, threadedly coupling the micro adjust screw to the door mounting plate via the threaded shaft, loosening the fastening screws and turning the micro adjust screw against said wall to cause the door mounting plate to slide horizontally along the hinge blade to provide door lift or rotation to compensate for flame or mounting misalignment; and
   tightening the fastening screws to lock the hinge blade to the door mounting plate.

11. The method of claim 10 wherein each of the slots for slidably receiving the fastening screws is inscribed in a channel formed in the bottom side of the door mounting plate, and each of the channels holds one of the captive nuts that thread onto the fastening screws.

12. The method of claim 11 wherein the channels in the bottom side of the door mounting plate prevent the nuts that thread onto the fastening screws from turning as the fastening screws are tightened or loosened.

13. The method of claim 12 wherein the micro adjust screw has a head attached to the threaded shaft, the head of the micro adjust screw is adapted to receive an adjusting tool.

14. The method of claim 13 wherein the head of the micro adjust screw is accessible with an adjusting tool inserted between the hinge base and the hinge blade.

15. The method of claim 14 wherein the head of the micro adjust screw is not visible from the top of the hinge.

16. The method of claim 14 wherein the head of the micro adjust screw is accessible without disassembling the hinge.

17. The method of claim 15 wherein the micro adjust screw is threadedly coupled to a perpendicularly oriented protrusion which projects out from a surface of the door mounting plate.

18. The method of claim 17 wherein the perpendicularly oriented protrusion projects out from the top surface of the door mounting plate.

\* \* \* \* \*